(12) United States Patent
Temple (10) Patent No.: US 11,234,590 B2
(45) Date of Patent: Feb. 1, 2022

(54) MEASURING SENSITIVITY TO POLARIZED LIGHT

(71) Applicant: The University of Bristol, Bristol (GB)

(72) Inventor: Shelby Temple, Bristol (GB)

(73) Assignee: THE UNIVERSITY OF BRISTOL, Bristol (GB)

(*) Notice: Subject to any disclaimer, the term of this patent is extended or adjusted under 35 U.S.C. 154(b) by 86 days.

(21) Appl. No.: 16/073,578

(22) PCT Filed: Feb. 1, 2017

(86) PCT No.: PCT/GB2017/050249
§ 371 (c)(1),
(2) Date: Jul. 27, 2018

(87) PCT Pub. No.: WO2017/134433
PCT Pub. Date: Aug. 10, 2017

(65) Prior Publication Data
US 2019/0029510 A1    Jan. 31, 2019

(30) Foreign Application Priority Data
Feb. 5, 2016   (GB) ..................................... 1602068

(51) Int. Cl.
*A61B 3/06* (2006.01)
*A61B 3/00* (2006.01)
*G02B 27/28* (2006.01)

(52) U.S. Cl.
CPC ............. *A61B 3/063* (2013.01); *A61B 3/0008* (2013.01); *A61B 3/06* (2013.01); *G02B 27/286* (2013.01); *G02B 27/288* (2013.01)

(58) Field of Classification Search
CPC ......... A61B 3/063; A61B 3/0008; A61B 3/06; G02B 27/286; G02B 27/288
See application file for complete search history.

(56) References Cited

U.S. PATENT DOCUMENTS

| 3,464,407 A | 9/1969 | Larson et al. |
| 3,481,330 A | 12/1969 | Cuppers et al. |

(Continued)

FOREIGN PATENT DOCUMENTS

| CN | 2875382 Y | 3/2007 |
| CN | 203736163 U | 7/2014 |

(Continued)

OTHER PUBLICATIONS

United Kingdom Intellectual Property Office; Search report dated Aug. 3, 2016 of Great Britain Patent Application No. 1602068.7, 3 pages.

(Continued)

*Primary Examiner* — Jack Dinh
(74) *Attorney, Agent, or Firm* — Shumaker, Loop & Kendrick, LLP; Patrick B. Horne (57) ABSTRACT

Embodiments test a subject's vision. A polarization arrangement polarizes incident light and rotates an angle of polarization applied to the incident light about an axis substantially collinear with a path of the light. An optical component directs light onto the polarization arrangement and produces light having a selected degree of polarization and having a rotating angle of polarization for observation by the subject The subject may be able to observe the visual phenomenon known as Haidinger's brushes and due to the rotation of the angle of polarization the eye's tendency to adapt away the phenomenon is counteracted, so that the effect persists and a more reliable testing of the subject can be carried out. Testing the subject's ability to perceive the phenomenon at multiple selectable degrees of polarization enables an assessment of the subject's eyes, and an estimate of macular pigment optical density and susceptibility to age-related macular degeneration.

24 Claims, 7 Drawing Sheets

(56) References Cited

U.S. PATENT DOCUMENTS

| | | | |
|---|---|---|---|
| 5,444,504 | A | 8/1995 | Kobayashi et al. |
| 6,556,853 | B1 | 4/2003 | Cabib et al. |
| 2003/0223064 | A1 | 12/2003 | Anderson et al. |

FOREIGN PATENT DOCUMENTS

| | | |
|---|---|---|
| CN | 204671376 U | 9/2015 |
| GB | 862823 | 3/1961 |
| GB | 2521443 | 6/2015 |
| JP | H02218333 A | 8/1990 |
| JP | H0-031076 A | 2/1993 |
| JP | H06165756 A | 8/1994 |
| JP | H08500049 A | 1/1996 |
| JP | 2002207122 A | 7/2002 |
| WO | 2007119592 A1 | 10/2007 |
| WO | 2015092428 A1 | 6/2015 |

OTHER PUBLICATIONS

Patent Cooperation Treaty; International Search Report dated Apr. 3, 2017 of PCT/GB2017/050249, 5 pages.
Patent Cooperation Treaty; Written Opinion dated Apr. 3, 2017 of PCT/GB2017/050249, 5 pages.
Temple SE et al, 'Perceiving polarization with the naked eye: characterization of human polarization sensitivity', Published Jan. 7, 2015, Proceedings of the Royal Society B, 282: 20150338. Available from: http://dx.doi.org/10.1098/rspb.2015.0338 [accessed Mar. 8, 2016], Whole document relevant, but see especially pp. 2-4; 9 pages.
Jul. 24, 2020 Office Action issued in Chinese Patent Application No. 201780009927.3 (20 pages).
Chinese Patent Office; Office Action received in Chinese Patent Application No. 100088 dated Jan. 13, 2021; 8 pages updated—resubmitted Chinese Office Action with translation, cited in correct Chinese Patent Application 201780009927.3 dated Jan. 13, 2021; 8 pages.
Japanese Patent Office; Office Action received in Japanese Patent Application No. 2018-533908 dated Dec. 1, 2020.
Chinese Patent Office; Office Action received in Chinese Patent Application No. 100088 dated Jan. 13, 2021; 8 pages.
Australia Patent Office; Office action received in Australian Patent Application No. 2017215280, dated Dec. 4, 2020; 5 pages.
Rothmayer, et al; Applied Optics, Oct. 10, 2007, vol. 46, No. 29, Xavier University, Cincinnati, Ohio 45207; "Nonlinearity in the rotational dynamics of Haidinger's brushes"; pp. 7244-7251.
Phillip L. Muller et al.; Department of Ophthalmology, University of Bonn, Bonn, Germany Center for Rare Diseases, University of Bonn, Bonn, Germany "Perception of Haidinger Brushes in Macular Disease Depends on Macular Pigment Density and Visual Acuity" IOVS j Mar. 2016 j vol. 57 j No. 3; pp. 1448-1456.
India Patent Office; Examination Report Under Sections 12 & 13 of the Patents Act, 1970 and the Patents Rules 2003, cited in Indian Application No. 201817030945 dated Sep. 21, 2021; 7 pages; partial English translation included.

MEASURING SENSITIVITY TO POLARIZED LIGHT

TECHNICAL FIELD

The present disclosure relates to the fields of optometry and ophthalmology. More particularly it relates to measuring sensitivity to the polarization of light.

BACKGROUND

Humans can perceive the polarization of light, although we are typically unaware of our ability to do so. In particular, we detect the angle of polarization by means of an entoptic visual phenomenon known as Haidinger's brushes. The phenomenon was first described by Wilhelm Karl von Haidinger in 1844. He reported that humans perceive a faint pattern of yellow and blue bowtie-like shapes that intersect at the viewer's point of fixation when viewing a polarized light field, with no spatial variation in intensity or colour. Note that herein the term polarized light is used to refer to linearly polarized light and where circular or elliptical polarization is meant this will be explicitly stated. The mechanism mediating human polarization sensitivity is understood to be dependent on the presence of dichroic carotenoid pigments found in the macula, which have an average orientation perpendicular to the Henle fibres that radiate from the centre of the fovea. The macular pigments, which give the macula lutea its yellow colour, have a spectral absorbance that peaks at 458 nm, which matches the maximum sensitivity for Haidinger's brushes (peak at 460 nm). The role of the macula in producing Haidinger's brushes has led to investigation of the phenomenon as a potential approach for screening for central visual field dysfunction, including congenital abnormalities of the macula, some forms of colour blindness, macular edema, strabismus and amblyopia. Moreover, the correlation between low macular pigment density and the risk of developing age related macular degeneration (AMD) means that polarization-based testing offers the potential for a simple means of identifying those at risk of, for example, AMD and monitoring disease progression.

SUMMARY

In at least some embodiments the present techniques provide an apparatus for testing a subject's vision comprising: a polarization arrangement configured to polarize incident light and rotate an angle of polarization applied to the incident light about an axis substantially collinear with a path of the incident light; and an optical component configured to direct light onto the polarization arrangement, wherein the polarization arrangement is configured to produce light having a selected degree of polarization from multiple selectable degrees of polarization and having a rotating angle of polarization for observation by the subject. The present techniques recognise the potential for testing a subject's vision by means of an assessment of their ability to perceive Haidinger's brushes when presented with polarized light, yet also further recognise that the typically transient nature of human perception of Haidinger's brushes (since the human visual system tends to adapt this subtle phenomenon away after approximately 5 seconds) presents a challenge when performing this testing. However, the inventor of the present techniques has realised that an improved mechanism for testing a subject's vision may be provided by causing the angle of polarization of the polarized light presented to the subject to rotate, wherein this rotation is about an axis which is substantially collinear with a path of the polarized light, because this rotation of the angle of polarization means that the eye does not (or at least does not so easily) adapt away the Haidinger's brushes phenomenon. Moreover, since the human cornea is birefringent (the amount of birefringence varying between individuals) if the alignment of the polarization happens to match one of the axes of birefringence this can affect the degree of linear polarization, which would be undesirable in the present context. The rotation of the angle of polarization advantageously mitigates against this phenomenon. A more reliable mechanism for testing a subject's vision is therefore provided, wherein the transient nature of the Haidinger's brushes effect is reduced, meaning that a range of subjects can be tested, with there being less dependency on a particular subject's ability to adapt away this phenomenon.

Moreover, the inventor of the present techniques has further found that useful information about a subject's vision may be derived not only from an assessment of their ability to perceive polarization, but also from the degree of polarization, i.e. ranging from 0% polarization (entirely unpolarized) to 100% polarization (fully polarized), which the subject is able to perceive. Accordingly, the polarization arrangement of the apparatus is configured not only to polarize the incident light, but also such that the degree of polarization generated can be selected from multiple degrees of polarization. Thus, in operation when testing a subject's vision, a chosen degree of polarization is applied to the incident light, such that the subject is presented with polarized light having a selected degree of polarization, wherein the angle of polarization rotates whilst being observed by the subject. Further, it is to be noted that an advantageous synergy is provided by the rotation of the angle of polarization of the light presented to the subject together with the selection of the degree of polarization of the light, since rotating the angle of polarization facilitates the perception of the Haidinger's brushes phenomenon, even at lower degrees of polarization, because the continually changing presentation of the angle of the Haidinger's brushes mitigates against the eye's tendency to adapt the effect away. A subject may therefore be more reliably tested for their ability to perceive this phenomenon at a range of degrees of polarization.

In some embodiments the polarization arrangement comprises a rotation direction selection mechanism to select a direction of rotation of the angle of polarization. The inventor of the present techniques has further realised that not only is it advantageous to rotate the angle of polarization applied to the light which the subject observes, since the rotation of the polarization maintains the Haidinger's brushes phenomenon in the subject's vision, but has further realised that an advantageously simple and effective method for determining if the subject can perceive the Haidinger's brushes phenomenon is to ask the subject to identify the direction in which the brushes are rotating. In this context it should be appreciated that the Haidinger's brushes effect is relatively subtle, even at full polarization, and therefore a technique such as this which facilitates the testing for the subject is of notable benefit. Accordingly, the rotation direction selection mechanism enables the operator of the apparatus (who may, for example, be an ophthalmologist or optometrist testing the subject's vision) to select the direction of rotation and then simply to ask the subject to name the direction.

In such an arrangement where the direction of rotation can be selected, the selection of the direction of rotation may be implemented in a number of ways. In some embodiments the rotation direction selection mechanism comprises a user input to select the direction of rotation. This enables the user (e.g. the above-mentioned ophthalmologist or optometrist) to choose the direction of rotation. Alternatively, or in addition, in some embodiments the rotation direction selection mechanism is configured to select the direction of rotation according to at least one of: a predetermined sequence of directions of rotation; and a randomly chosen direction of rotation. Accordingly, the configuration of the rotation direction selection mechanism can provide that in a sequence of tests of the subject's vision (which may be for the same degree of polarization or for a sequence of degrees of polarization) the direction of rotation used for each test can change in a manner which the subject cannot predict and confidence that they have correctly perceived the direction of rotation rather than merely guessing is gained.

In some embodiments the polarization arrangement comprises: a rotatable polarizer; and a depolarization arrangement, wherein the depolarization arrangement comprises multiple depolarization filters and is configured to enable a selected depolarization filter of the multiple depolarization filters to be selected and positioned in the light path to generate the selected degree of polarization. Accordingly, the polarization arrangement may essentially be provided in two parts, namely firstly a portion that polarizes the incident light and rotates, such that light having a rotating angle of polarization is generated, and secondly the depolarization arrangement that enables a selected degree of depolarization to be applied to the polarized light to reduce the degree of polarization by a selected amount, thus providing the selected degree of polarization. Importantly, it should be noted that the use of such depolarization filters therefore enables the degree (per cent) of linear polarization of the light to be selectively reduced, whilst not adding any circular polarization. The inventor of the present techniques realised that this is advantageous in the present context because the human cornea is birefringent and the amount of birefringence varies between individuals. At certain orientations circular polarization becomes partially linear as it passes through the cornea thus (undesirably here) altering the degree of linear polarization.

The depolarization filters may take a variety of forms, but in some embodiments the multiple depolarization filters are arranged in a substantially circular pattern and the depolarization arrangement is configured to be rotated to bring the selected depolarization filter of the multiple depolarization filters into the light path. Thus, the depolarization filters may for example be positioned such that each lies around the periphery of a (imaginary) circle, for example forming part of a larger disc into which the multiple depolarization filters are embedded. Rotation of the larger disc then enables one of the multiple depolarization filters to be "selected" by bringing it into a predetermined position, in particular in the light path of the polarized light, such that the selected depolarization may be applied to the polarized light.

The multiple depolarization filters may be provided in a number of ways, but in some embodiments the multiple depolarization filters each comprise a distribution of particles in a translucent plastic carrier. This manner of providing the depolarization filters enables the degree of depolarization applied by each filter to be easily and reliably set, in particular by varying the density of the particles that are distributed in the translucent plastic carrier, such that a corresponding varying degree of multiple elastic scattering occurs when light is transmitted by the filter, and hence a corresponding degree of depolarization occurs. Moreover, this approach also simplifies the apparatus with respect to alternative depolarization filter techniques in which the translucent medium is provided by a fluid (such as water), which must then be continually stirred or agitated to provide a constantly even distribution of particles suspended within it.

In some embodiments the particles have a mean particle size between 100 nm and 2000 nm. The size of the particles is chosen to ensure that light that traverses the filter undergoes multiple elastic scattering events to depolarize it. The particles themselves may take a variety of forms, but in some embodiments the particles comprise (spheres of) dielectric material and may in particular comprise hollow glass spheres. Hollow glass spheres are conveniently neutrally buoyant in the carrier and thus easier to keep well mixed and evenly spread. The translucent plastic carrier may also take a variety of forms, but in some embodiments is formed of a cured polyester resin. The carrier appears translucent due to the multiple light scattering events. It is advantageous to use a polyester resin, as opposed to other varieties of plastic such as polyvinyl, because of the avoidance of stress patterns in the plastic, which could affect the polarization of the light being passed through the depolarization filter.

Other techniques for providing the multiple depolarization filters may also be used, such as varying degrees of frosting or sandblasting glass, or using low grade polarizers that are intentionally made to a lower specification by changing the amount or consistency of the diattenuation in the material.

It is, however, not necessary for the polarization arrangement to be provided in separate parts in the manner discussed above, and accordingly in some embodiments the polarization arrangement comprises multiple polarization filters, wherein the multiple polarization filters provide the multiple selectable degrees of polarization, and is configured for a selected polarization filter of the multiple polarization filters firstly to be selected and positioned in the light path and secondly to be rotated while under observation by the subject. In other words, rather than polarizing the light (essentially fully) and then using one of the depolarization filters described above to reduce the degree of polarization to the desired amount, each polarization filter can be provided to directly cause a selected degree of polarization to be applied to the incident light and by rotation of this selected polarization filter the light having the rotating angle of polarization with the selected degree of polarization is thus provided in one step. The material of such polarization filters is therefore selected to cause polarization of the light to the selected degree.

Other techniques may be used to produce the light having the selected degree of polarization and in some embodiments the apparatus further comprises: a light combining component; and a further optical component configured to direct light onto the light combining component; wherein the optical component and the further optical component each further comprise a light intensity selection mechanism to cause the light combining component to produce the light having the selected degree of polarization. Accordingly, the light combining component receives light: a) coming from the optical component that directs light onto the polarization arrangement, which in turn provides the polarized light to the light combining component; and b) from a further optical component (which provides non-polarized light). Furthermore, the provision of a light intensity selection mechanism for each of the optical component and the further optical component thus enables the finally produced light to have the selected degree of polarization, by combination of appropriate amounts of polarized and non-polarized light. The light intensity selection mechanism may be an electronic variation of the light intensity generated by, say, an LED source, may be an interposed variable filter, and so on.

The optical component itself which directs light onto the polarization arrangement may take a variety of forms, and may for example be able to generate light itself, or merely to redirect light emanating from elsewhere. Accordingly, in some embodiments the optical component is a light source configured to generate light for direction onto the polarization arrangement. This may for example take the form of an LED source. The light source may be arranged to generate light with different ranges of wavelengths, depending on the particular implementation. In some embodiments the light source is configured to generate light within a wavelength range of 400 nm to 550 nm. Generally, Haidinger's brushes appear to have a yellow and blue-ish hue, but when observed in the context of light having this narrower range of wavelengths they can appear darker (vary in intensity rather than wavelength) to the human eye, which may facilitate their perception. Alternatively, in some embodiments the light source is configured to generate full spectrum light.

As mentioned above, the optical component may, however in some embodiments, not generate light itself, and may for example comprise a reflector configured to reflect light from an external source onto the polarization arrangement. This may for example be a mirror.

The manner in which the produced light is presented to the observer, i.e. the subject who is having their vision tested, may take a variety of forms, depending on the particular implementation of the apparatus. For example, it could be provided as a table-top device intended for use by an ophthalmologist or optometrist, or as a smaller, portable device intended to be used in a hand-held manner. However configured, in some embodiments the apparatus further comprises an observation component configured to receive polarized light from the polarization arrangement for observation by the subject. This observation component can then present the polarized light to the subject in a manner which facilitates its observation. For example, in some embodiments the observation component comprises a translucent panel. The provision of a panel such as this onto which the polarized light is projected may be advantageous for a number of reasons, for example because it presents the subject with a fixed point at which they must focus in order to make the observation, which is more easily observable. Moreover, the provision of such a panel may help to prevent the observer from seeing any physical rotation within the apparatus from which they might be able to derive the direction of rotation when this is asked for. For this purpose, the translucent panel may be slightly opaque or frosted. It should be appreciated that the opacity or frosting of this panel can only be relatively weak such that it does not significantly decrease the degree of polarization, which would impair the subject's ability to perceive the Haidinger's brushes, but nevertheless as mentioned above placing such a translucent panel as a last component in the light path means that the preceding components of the apparatus are at least partially obscured for the subject, and in particular this may help to avoid the subject observing the direction of rotation of the polarization from a rotating physical component of the apparatus, rather than from the light transmitted itself. In some embodiments the observation component comprises a lens, for example as part of an eyepiece in an optical component into which the subject looks.

The rotation of the angle of polarization may be provided in a number of ways and in some embodiments the polarization arrangement is configured to rotate the angle of polarization in a selected direction of continuous rotation. It is, however, not necessary for a continuous rotation to be provided and the polarization arrangement may instead be configured to rotate the angle of polarization back and forth between two predetermined angular orientations. To name just one arbitrary example, the angle of polarization could be rotated back and forth between a first angle of approximately +45° with respect to the horizontal and a second angle of approximately −45° with respect to the horizontal.

The rotation of the polarization arrangement may be effected in a number of ways and in some embodiments the polarization arrangement comprises a motor to drive the rotation. In other embodiments the polarization arrangement comprises a manually actuated mechanism to drive the rotation, for example in a handheld device this could take the form of a thumb wheel.

At least some embodiments provide a method of testing a subject's vision comprising the steps of: directing light onto a polarization arrangement; selecting a degree of polarization from multiple selectable degrees of polarization provided by the polarization arrangement; using the polarization arrangement to rotate an angle of polarization applied to incident light about an axis substantially collinear with a light path of the incident light; producing light having the selected degree of polarization and having a rotating angle of polarization for observation by the subject; and asking whether the subject can observe a rotating pattern consistent with Haidinger's brushes when using the selected degree of polarization.

In some embodiments, the method further comprises causing the polarization arrangement to rotate the angle of polarization in a selected direction of rotation; and asking the subject to report an observed direction of rotation of the rotating pattern and determining if the observed direction of rotation matches the selected direction.

In some embodiments, the method comprises iteratively testing the subject's vision by a process of a) firstly selecting a maximum degree of polarization as the selected degree of polarization from the multiple selectable degrees of polarization; b) iteratively lowering the degree of polarization and choosing the selected direction of rotation either randomly or according to a predetermined sequence of directions; and c) determining the lowest degree of polarization at which the subject was able to observe the rotating pattern and to correctly report the selected direction of rotation. Performing the iterative assessment from the maximum degree of polarization towards lower degrees of polarization provides a testing protocol that the subject may find easier, as they are essentially then determining when a known visible phenomenon disappears (assuming they can see it at maximum polarization), rather than when an unknown phenomenon appears (assuming that they cannot perceive it at the lowest degree of polarization that can be applied). However, the degree of polarization could be varied in either direction, or indeed degrees of polarization could be picked in a non-sequential order, which is unknown to the subject, to lend further confidence to the assessment of the subject's vision.

In some embodiments, the method further comprises a final step of estimating the subject's macular pigment optical density in dependence on the subject's ability to observe the rotating pattern consistent with Haidinger's brushes when using the selected degree of polarization.

Estimating the subject's macular pigment optical density may, in some embodiments, be further performed in dependence on the subject's ability to correctly report the selected direction of rotation when using the selected degree of polarization.

In some embodiments, estimating the subject's macular pigment optical density further comprises estimating the subject's susceptibility to age-related macular degeneration.

At least some embodiments provide an apparatus for testing a subject's vision comprising: means for rotating an angle of polarization applied to incident light about an axis substantially collinear with a path of the incident light; and means for directing light onto the means for rotating the angle of polarization, wherein the means for rotating the angle of polarization is configured to produce light having a selected degree of polarization from multiple selectable degrees of polarization and having a rotating angle of polarization for observation by the subject.

BRIEF DESCRIPTION OF THE DRAWINGS

The present techniques will be described further, by way of example only, with reference to embodiments thereof as illustrated in the accompanying drawings, in which.

DESCRIPTION OF EMBODIMENTS

Figure 1:
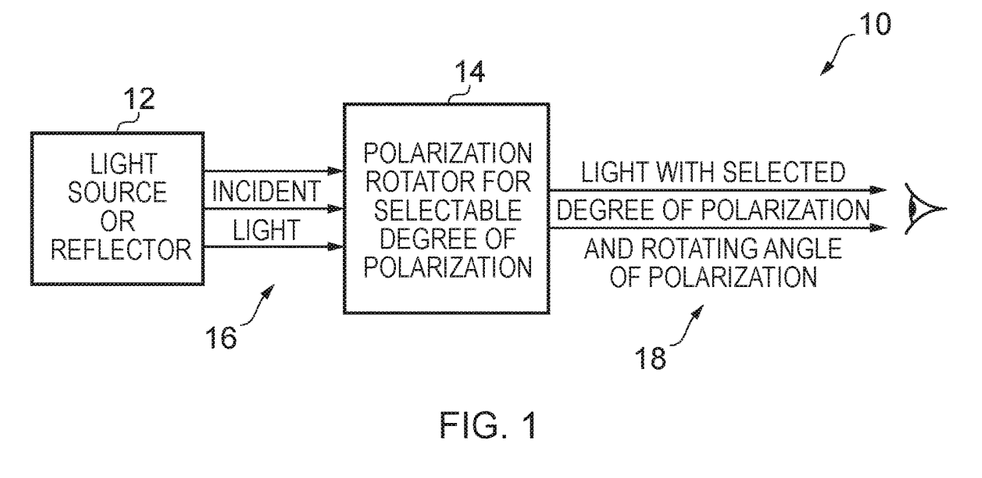
FIG. 1 schematically illustrates an apparatus in one example embodiment in which a polarization rotator is provided with which a selected degree of polarization can be applied to incident light.

FIG. 1 schematically illustrates an example embodiment of an apparatus 10 for testing a subject's vision. A light source (e.g. an LED light source) or reflector (e.g. a mirror) 12 casts incident light 16 onto a polarization rotator (rotating polarizer) 14, which allows a selected degree of polarization to be chosen by the user and applied to the incident light. More generally the polarization rotator 14, configured to both cause a rotating angle of polarization to be applied to the incident light and to allow the degree of that polarization to be chosen, is also referred to herein as a polarization arrangement. The rotation of the polarization is essentially around the direction in which the light travels, i.e. about an axis substantially collinear with the path of the light. The light 18 thus generated with a selected degree of polarization and rotating angle of polarization is observed by the subject being tested. Presentation of such polarized light to the subject enables the subject (assuming that their visual sensitivity to the polarization of light is adequate) to observe the entoptic visual phenomenon known as "Haidinger's brushes", namely a faint pattern of bowtie-like shapes that intersect at the viewer's point of fixation. When full-spectrum light is provided by the light source or reflector 12, these shapes have a faint yellow and blue appearance, although this appearance can be altered by generating light with (or filtering full spectrum light to have) a limited wavelength range. For example when light is generated within a wavelength range of approximately 400 nm to 550 nm, the shapes appear more "light and dark", and thus such a limited wavelength range may be chosen if this appearance is perceived more easily by the subjects being tested.

The mechanism provided to rotate the polarization of the light may take a variety of forms as will be discussed in more detail below with reference to the subsequent figures. However provided, generally the rotation of the polarization of the light means that the Haidinger's brushes visual phenomenon persists in the subject's vision, since it has been found that the eye only adapts away perception of the Haidinger's brushes when the angle of polarization is constant (i.e. the Haidinger's brushes do not rotate). In the context of testing a subject's vision the rotation of the angle of polarization of the light is therefore advantageous, since this avoids the subject having to perceive the phenomenon rather quickly (it is otherwise adapted away within a matter of seconds) and a more relaxed, and indeed reliable, testing procedure is thus provided.

Figure 2:
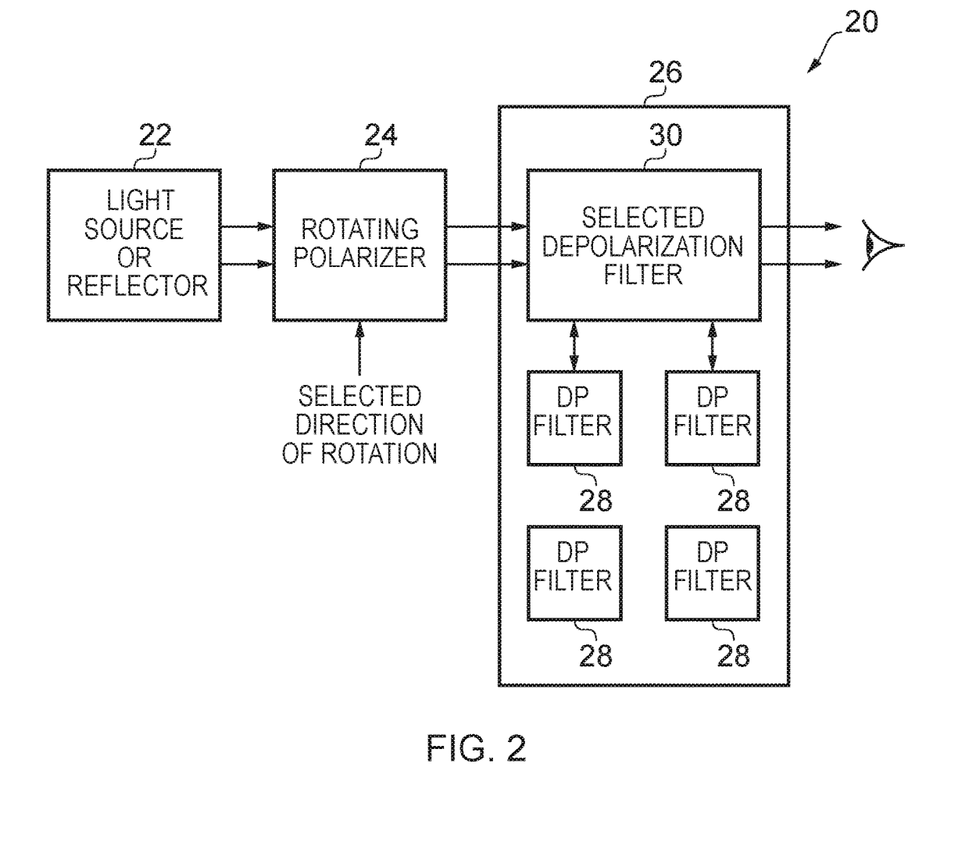
FIG. 2 schematically illustrates an apparatus in one example embodiment in which a selected depolarization filter can be brought into the path of light having a rotating polarization to reduce the degree of polarization by a chosen amount.

FIG. 2 schematically illustrates an example embodiment of an apparatus 20 for testing a subject's vision. The apparatus comprises a light source or reflector 22, such as is described above for the equivalent component 12 in FIG. 1. In this example embodiment the polarization arrangement is provided by a rotating polarizer 24 and a depolarization arrangement 26. The rotating polarizer 24 comprises an input by which a user can specify the direction of rotation. It should be noted, however, that it is not essential in this embodiment for the direction to be specified by the user (and this is in particular advantageous if the user and subject being tested are one and the same person) and a configuration (not explicitly illustrated) may also be provided in which the user input merely specifies "new direction of rotation" and a mechanism within the rotating polarizer 24 then determines what that new direction of rotation is (and of course it should be appreciated that this could be the same as the existing direction of rotation, so that the direction at each iteration is unpredictable to the subject, who must then genuinely perceive the direction to be able to name it). This mechanism could for example randomly select the direction or could choose the direction from a predetermined sequence of directions, which is sufficiently unpredictable to the subject.

The polarized light produced by the rotating polarizer 24 is then transmitted through the depolarization arrangement 26. The depolarization arrangement 26 comprises a number of depolarization (DP) filters 28, each providing a different level of depolarization, such that when one of them is chosen as the selected depolarization filter 30 and positioned in the light path the resulting light observed by the subject has a corresponding degree of polarization. Here it is assumed that the rotating polarizer 24 will essentially polarize the light to 100% (although strictly complete polarization is not essential and it could be slightly less), and thus the depolarization filters provided will enable the polarization of the light to be reduced across a range of degrees of polarization, which is useful for the purposes of assessing the subject's vision. Most fully therefore the multiple depolarization filters 28 can be provided to cover a range of degrees of polarization, which essentially fully spans 0% to 100% polarization, although the inventor of the present techniques has experimentally found that few individuals are capable of perceiving the Haidinger's brushes phenomenon at a degree of polarization much below 15%, and for the sake of reducing manufacturing costs, depolarization filters which provide a reduction in the degree of polarization to below, say, 10% may be dispensed with, in particular if the medical view is that an individual who can perceive the phenomenon at this low level of polarization may be categorised as having an essentially fully healthy eye. Various physical arrangements may be provided to enable the user of the apparatus to bring the selected depolarization filter into the light path, and indeed the physical arrangement may be rather user dependent in that the multiple depolarization filters may simply be available to the user to pick out of a set by hand and slot in and out of a predetermined position in the light path. However, the present techniques further provide convenient arrangements for the user, such as one in which the multiple depolarization filters are arranged in a circular fashion on a disc (examples of this being described below with reference to FIGS. 8 and 9), so that an appropriate rotation of the disc enables each depolarization filter to be positioned in the light path.

Figure 3:
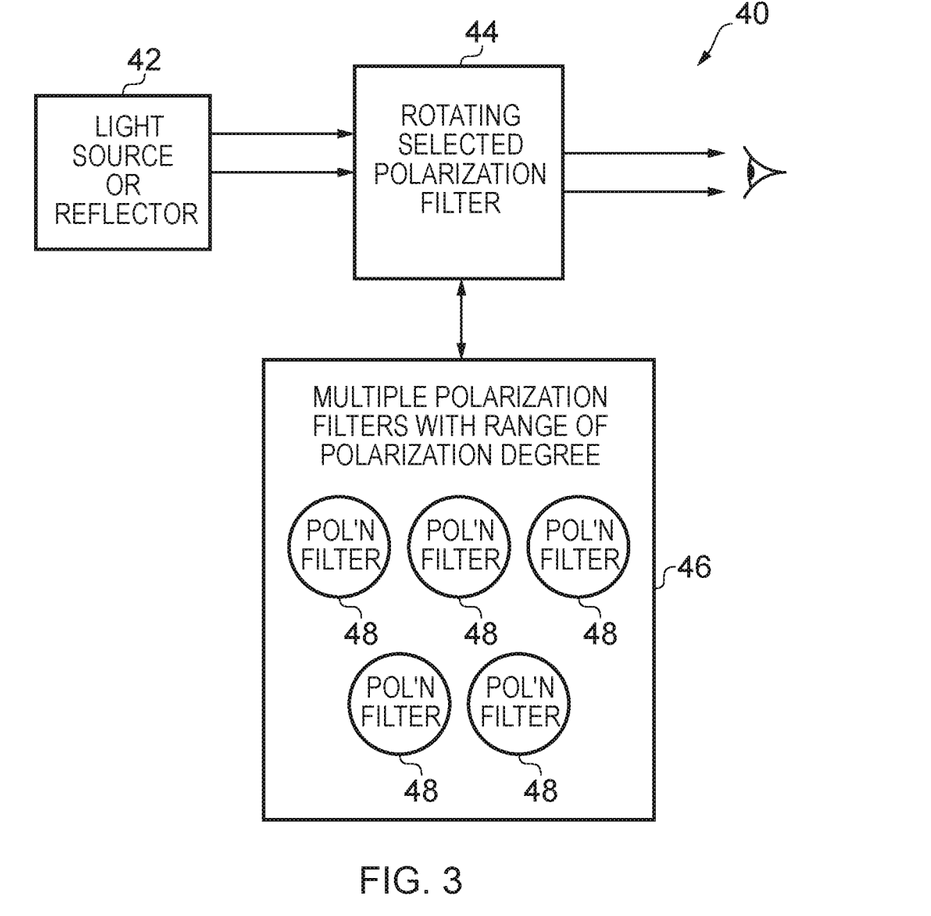
FIG. 3 schematically illustrates an apparatus in one example embodiment in which a selected polarization filter can be brought into the light path of incident light to both polarize the incident light with a selected degree of polarization and cause the angle of polarization to rotate.

FIG. 3 schematically illustrates an example embodiment of an apparatus 40 for testing a subject's vision. The apparatus comprises a light source or reflector 42, such as is described above for the equivalent component 12 in FIG. 1. In this example embodiment the polarization arrangement is provided by a rotating polarizer 44, for which a polarization filter is selected from the set 46 of multiple polarization filters 48 that provide a range of degrees of polarization. In other words, in this example embodiment the modification of the incident light received from the light source or reflector 42 occurs in one step in a single filter. As such, the polarization filters 48 are each formed of a selected material, which polarizes the light to the desired degree, thus providing the opportunity to provide the required range of degrees of polarization (as described above with reference to FIG. 2). The mechanism by which the selected polarization filter in such an example embodiment is brought into the light path may take a variety of forms, but it is recognised here that where the selected polarization filter needs to be rotated after having been positioned in the light path a trade off needs to be struck between the complexity of the mechanism (and its associated costs) and ease-of-use for the user. In order to provide an apparatus with relatively low manufacturing cost, the selection mechanism may essentially be manual in that a set 46 of multiple polarization filters 48 are available to the user, who can then manually select one and position it in the light path, before it is then rotated by either an automated mechanism (e.g. an electronically controlled motor) or a manual mechanism (e.g. a thumbwheel operated by the user).

Figure 4:
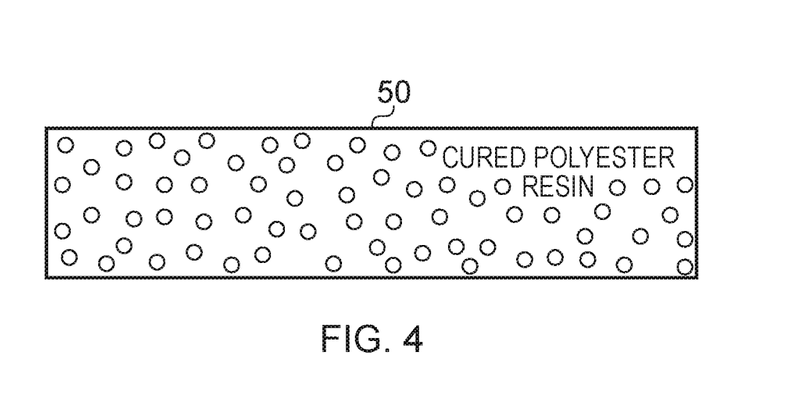
FIG. 4 schematically illustrates in cross-section a depolarization filter in one example embodiment.

FIG. 4 schematically illustrates in cross-section a depolarization filter 50 in one example embodiment. Here the supporting carrier material is a cured polyester resin and within it are embedded hollow glass spheres, represented by the small circles in the figure. In this example embodiment these hollow glass spheres have a mean diameter of 10 μm (supplied by Dantec Dynamics Ltd). The depolarization provided by the filter 50 is dependent on the density of particles (i.e. the hollow glass spheres), where it will be understood that a greater density of particles results in a greater degree of depolarization. The fact that the particles are embedded in a cured resin means that the stirring or agitation associated with suspending particles in a fluid to maintain a constantly even distribution of the particles is avoided. Furthermore, the selection of a polyester plastic (as opposed to, for example, a polyvinyl plastic) provides a non-distorting background medium, in which stress patterns, which could affect the polarization, are avoided. Significantly, these custom designed filters also advantageously enable the degree of polarization to be changed (decreased) without changing the ellipticity of the polarized light. This is important in the present context because the human cornea is birefringent and the amount of birefringence varies between individuals. At certain orientations circular polarization becomes partially linear as it passes through the cornea, thus (undesirably here) altering the degree of linear polarization.

A range of such depolarization filters may therefore be easily produced according to the present techniques, by thoroughly mixing a predetermined amount (for example by weight) of particles into a prepared uncured (i.e. still fluid) resin within a mould, shortly before the resin cures. The selection of the size of the particles (in this example embodiment the hollow glass spheres) is also of significance and according to the present techniques a mean particle size greater than 700 nm (i.e. approximately the upper wavelength limit of visible light) may be chosen with the particles of a specific density, such that the light undergoes multiple elastic scattering events to depolarize the transmitted light.

Figure 5:
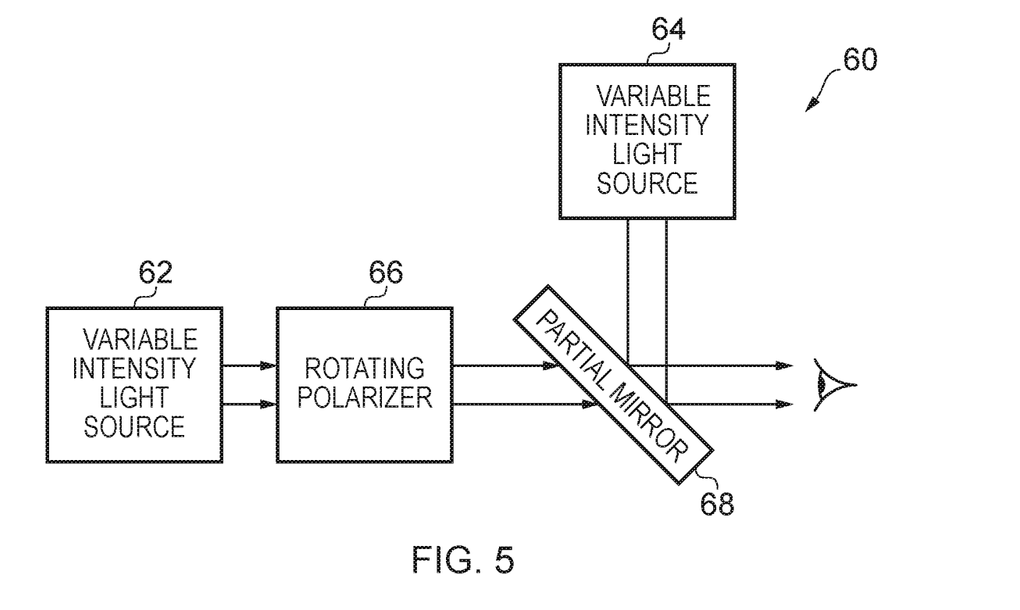
FIG. 5 schematically illustrates an apparatus in one example embodiment in which polarized light from a first variable intensity light source and non-polarized light from a second variable intensity light source are combined by a partial mirror.

FIG. 5 schematically illustrates an example embodiment of an apparatus 60 for testing a subject's vision. In this arrangement, two light sources 62 and 64 are provided, which in the manner described above may in fact be true light sources such as LED sources or merely reflectors such as mirrors. In addition, each of the light sources 62 and 64 comprises an intensity selection mechanism, so that the intensity of light produced by each source can be chosen by the user of the apparatus. This light intensity selection mechanism may for example be provided by electronic control of an LED source or by applying a variable filter. Light produced by the variable intensity light source 62 is incident on the rotating polarizer 66 and the light produced by the rotating polarizer 66 is incident on the partial mirror 68. Light produced by the variable intensity light source 64 is directly incident on the partial mirror 68 (on its opposite side). The partial mirror 68 combines the light received from each source for observation by the subject being tested. In essence therefore the light from the variable intensity light source 64 is unpolarized whilst the light received from the variable intensity light source 62 and the rotating polarizer 66 is polarized. By setting the respective intensities of light produced by the sources 62 and 64, the user is therefore able to control the degree of polarization of the light observed by the subject.

Figure 6A:
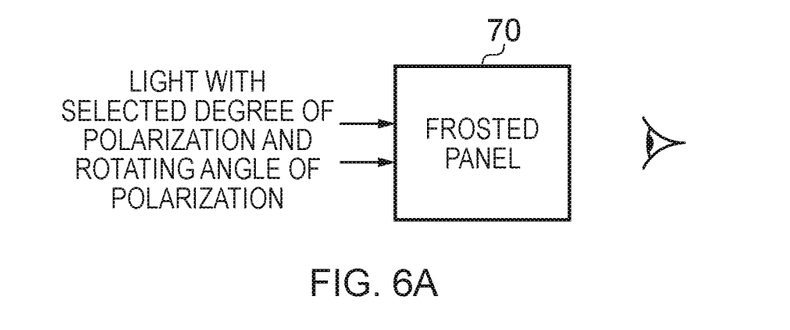
FIG. 6A schematically illustrates the use of a frosted panel for observation by the subject being tested in one example embodiment.
Figure 6B:
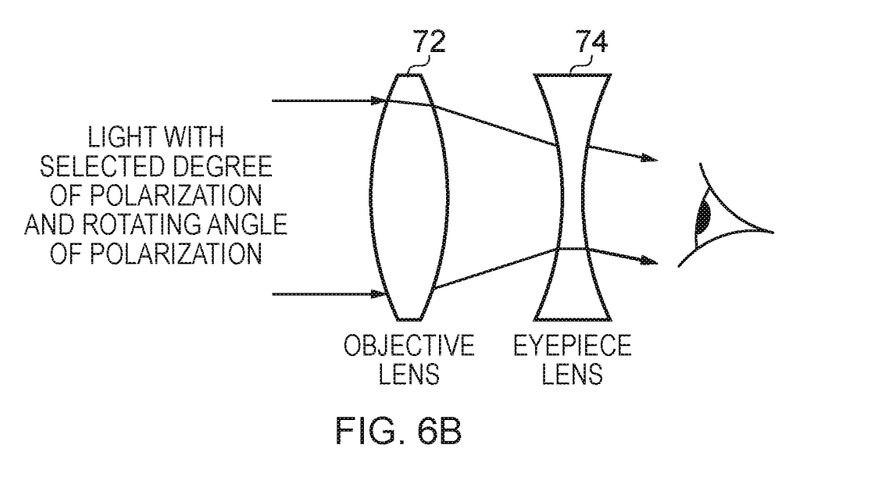
FIG. 6B schematically illustrates the use of an objective lens and eyepiece lens to assist observation by the subject being tested in one example embodiment.

FIGS. 6A and 6B schematically illustrates two example ways in which the light produced according to the present techniques (i.e. having a selected degree of polarization and a rotating angle of polarization) may be presented to the subject being tested. In the example of FIG. 6A the light produced (for example from the preceding parts of the apparatus in one of the arrangements described above with respect to the preceding figures) is directed on to a lightly frosted (i.e. translucent, or clouded) panel 70. It will be appreciated that the frosting of this panel can only be relatively weak such that it does not significantly impair the subject's ability to perceive the Haidinger's brushes, but nevertheless placing such a frosted panel as a last component in the light path means that the preceding components of the apparatus are at least partially obscured for the subject, and in particular this may help to avoid the subject observing the direction of rotation of the polarization from a rotating physical component of the apparatus, rather than from the light transmitted itself. FIG. 6B shows an example in which light produced according to one or more of the above described techniques is presented to the subject through a pair of lenses, namely objectives lens 62 and eyepiece lens 74, which together form an observation eyepiece. It will be appreciated that the number and form of these lenses may take a variety of forms in dependence on the context in which they are implemented (taking into account the distance to the subject's eye, the desired simplicity of the lens arrangement, and so on).

Figure 7A:
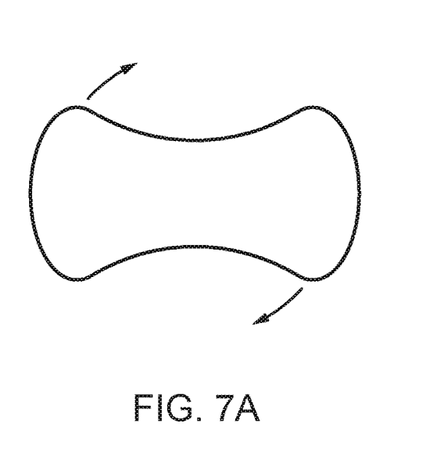
FIG. 7A schematically illustrates Haidinger's brushes continually rotating in one direction in one example embodiment.
Figure 7B:
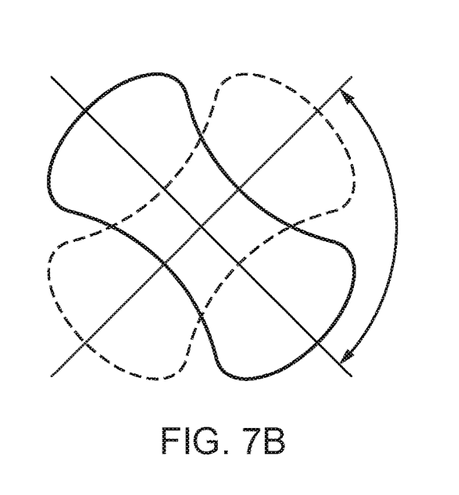
FIG. 7B schematically illustrates Haidinger's brushes rotating back and forth between two angular orientations in one example embodiment.

FIGS. 7A and 7B schematically illustrate two ways in which Haidinger's brushes may be presented to the subject being tested. FIG. 7A shows an example in which the rotating polarizer rotates in a single continuous direction (for each iteration, i.e. degree of polarization, of the testing procedure) and hence the Haidinger's brushes phenomenon observed also rotates in a single continuous direction. FIG. 7B shows an example in which the rotating polarizer rotates backwards and forwards between two predetermined angular orientations and hence the Haidinger's brushes phenomenon observed also rotates backwards and forwards between two angular orientations. If the example of FIG. 7B is used in a testing procedure where the subject is asked to name the direction of rotation, the speed of angular rotation may be selected to be sufficiently slow that the subject is able to name the direction as brush pattern moves in one of the directions. It is to be noted that in general (i.e. whichever particular configuration of an apparatus according to the present techniques is being used) there is flexibility in the speed at which the rotating polarizer is configured to rotate, although it should be understood that the rotation should be sufficiently fast that the eye is not able to adapt away the Haidinger's brushes phenomenon and equally should be sufficiently slow that the subject is still able to observe the phenomenon.

Figure 8:
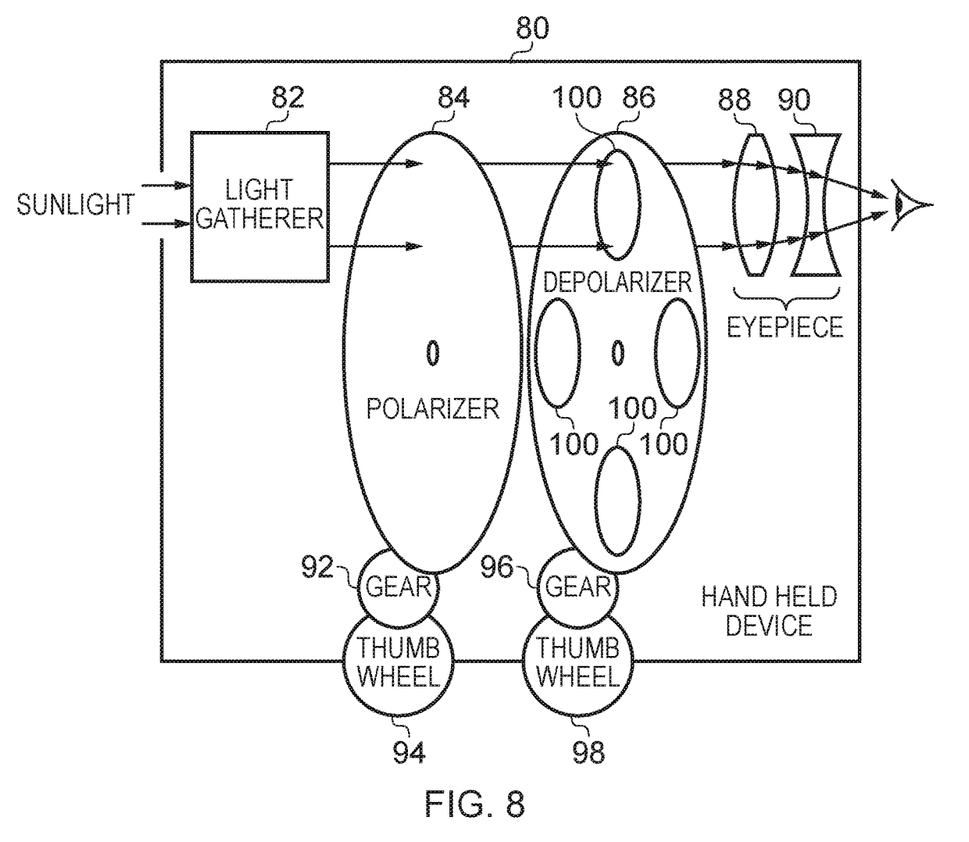
FIG. 8 schematically illustrates the internal configuration of a handheld device in one example embodiment.

FIG. 8 schematically illustrates an apparatus in one example embodiment that is provided as hand held device 80. One motivation behind this particular configuration is to provide a device that is cheaply manufactured and portable, and hence it is envisaged that the original source of the light used is sunlight, although this is not essential and for example a small battery-powered LED light source could also be used. The components of the handheld device 80 shown in FIG. 8 are the light gather 82 (for example one or more lenses), a polarizer wheel 84, a depolarizer wheel 86, and an eyepiece consisting of an objective lens 88 and an eyepiece lens 90. The gear wheel 92 and a thumb wheel 94, wherein the thumb wheel 94 is partially exposed to the outside of the handheld device 80 to provide a mechanism for the user to manually cause the rotation of the polarizer wheel 84. It will be understood that the nature of the material of the polarizer wheel 84 is provided such that rotation of the wheel also causes rotation of the angle of polarization of the light it produces. In a variation on the configuration illustrated in FIG. 8, the light received by the polarizer wheel 84 from the light gatherer 82 may be incident relatively centrally on the polarizer wheel 84, such that only a relatively simple structure of the polarizing material of the polarizing wheel must be provided. The depolarizer wheel 86 is similarly provided with an associated gear wheel 96 and thumb wheel 98, such that the user can cause rotation of the depolarizer wheel 86. This rotation serves a different purpose namely to bring one of the depolarization filters 100 into the light path, such that a selected strength of depolarization can be used and consequently a selected degree of polarization of the light passing through the eyepiece to the subject being tested can be selected.

Figure 9:
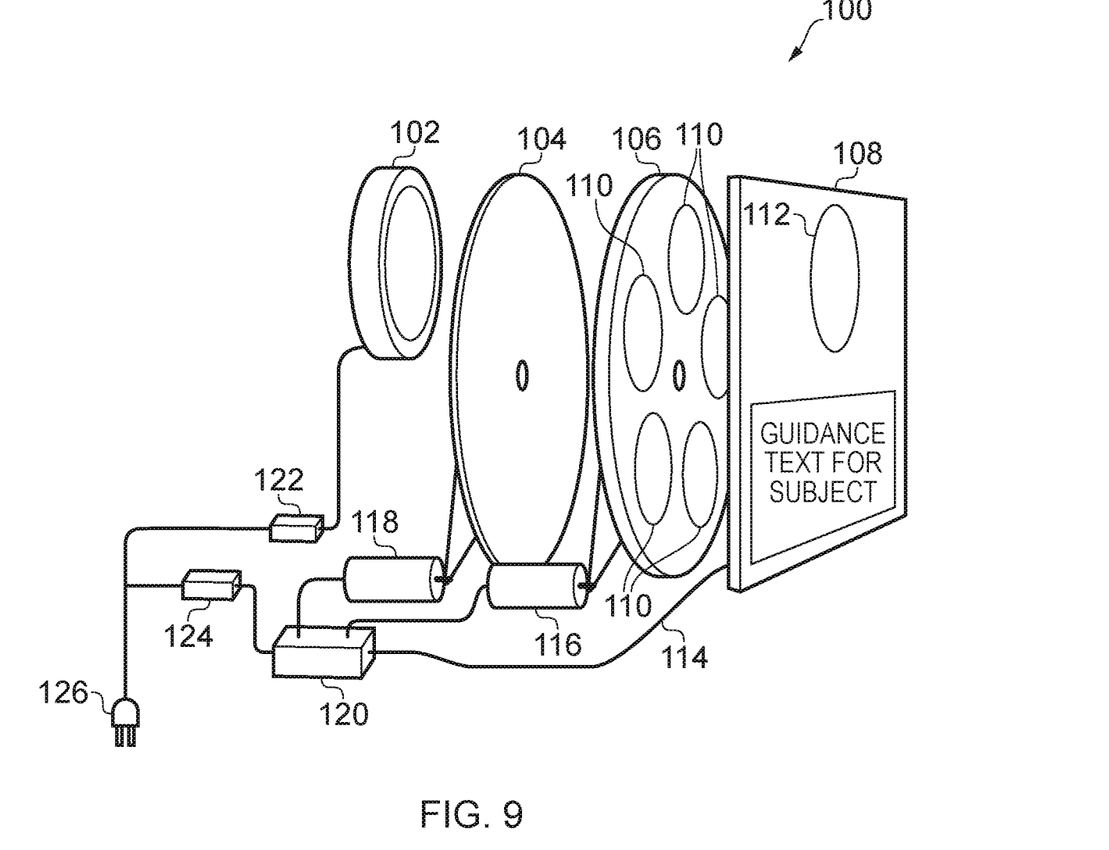
FIG. 9 schematically illustrates the internal configuration of a table-top device in one example embodiment.

FIG. 9 shows a perspective illustration of an apparatus 100 for testing a subject's vision in one example embodiment. The components shown on the light path are an LED flat panel light 102, a rotating polarizer wheel 104, a depolarizer wheel 106, and a fully opaque wall 108 with an opening 112 and rear illuminated text for guiding the subject. Also shown is a power lead 114 to provide power for LEDs in the opaque wall 108, which illuminate the guidance text for the subject, a small DC motor 116 to drive the depolarizer wheel 106, a small DC motor 118 to drive the polarizer wheel 104, and a microcontroller 120 (for example such as an Arduino or Raspberry Pi) to provide control for the motors 116 and 118 and of the illumination of the text in the wall 108. This microcontroller 120 also determines the direction of rotation of the polarizer wheel 104 and this control may be set to cause the direction to be randomly selected at each iteration or selected from a predetermined sequence of directions. A transformer 122 for the LED panel 102, a transformer 124 for the microcontroller 120, and a mains AC plug 126 are also shown.

Figure 10:
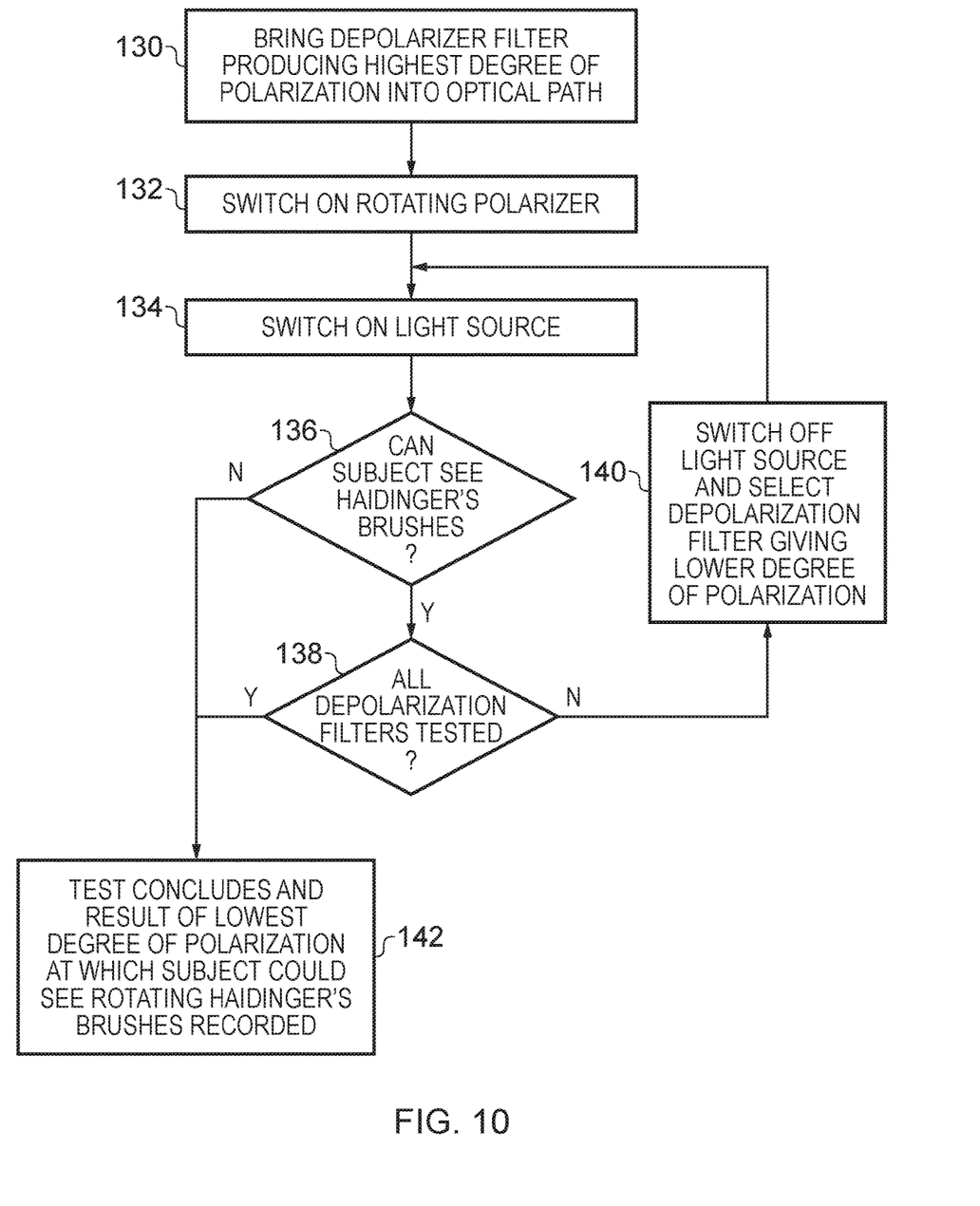
FIG. 10 shows a sequence of steps that are carried out according to the method of one example embodiment.

FIG. 10 shows a sequence of steps that are carried out according to one example embodiment of a method according to the present techniques. These steps will typically be carried out in part by a user of the apparatus and in part under the automated control of, say, a microcontroller such as item 120 in FIG. 9. The flow begins at step 130 where a depolarization filter producing the highest degree of polarization available in the system is brought into the optical path. Of course it should be appreciated that in effect this may not be a true "depolarization" filter if the aim is to produce as close to maximum polarization as possible and the depolarization filter selected at this first iteration of testing may essentially be transparent to the transmitted light. At step 132 the rotating polarizer is switched on and then at step 134 the light source (in this example the LED panel 102 shown in FIG. 9) is switched on. It is then determined by enquiry at step 136 if the subject can see Haidinger's brushes. If they can, then the flow proceeds to step 138 where it is determined if all depolarization filters available in the apparatus have been tested. Of course at the first iteration this is unlikely to be the case because multiple depolarization filters are typically provided. If more depolarization filters are available then the flow continues to step 140, where the light source is switched off and a new depolarization filter is selected (and brought into the light path) giving a lower degree of polarization. The flow then returns to step 134, where the light source is switched on again, and it is then determined again at step 136 if the subject can see Haidinger's brushes at this new, lower degree of polarization. This iterative process around the loop of steps 134, 136, 138 and 140 continues until the subject reports at step 136 that they can no longer see Haidinger's brushes or there are no further available depolarization filters at step 138. The flow then proceeds to step 142 where the test concludes and the result of the lowest degree of polarization at which the subject could see the rotating Haidinger's brushes is recorded.

Figure 11:
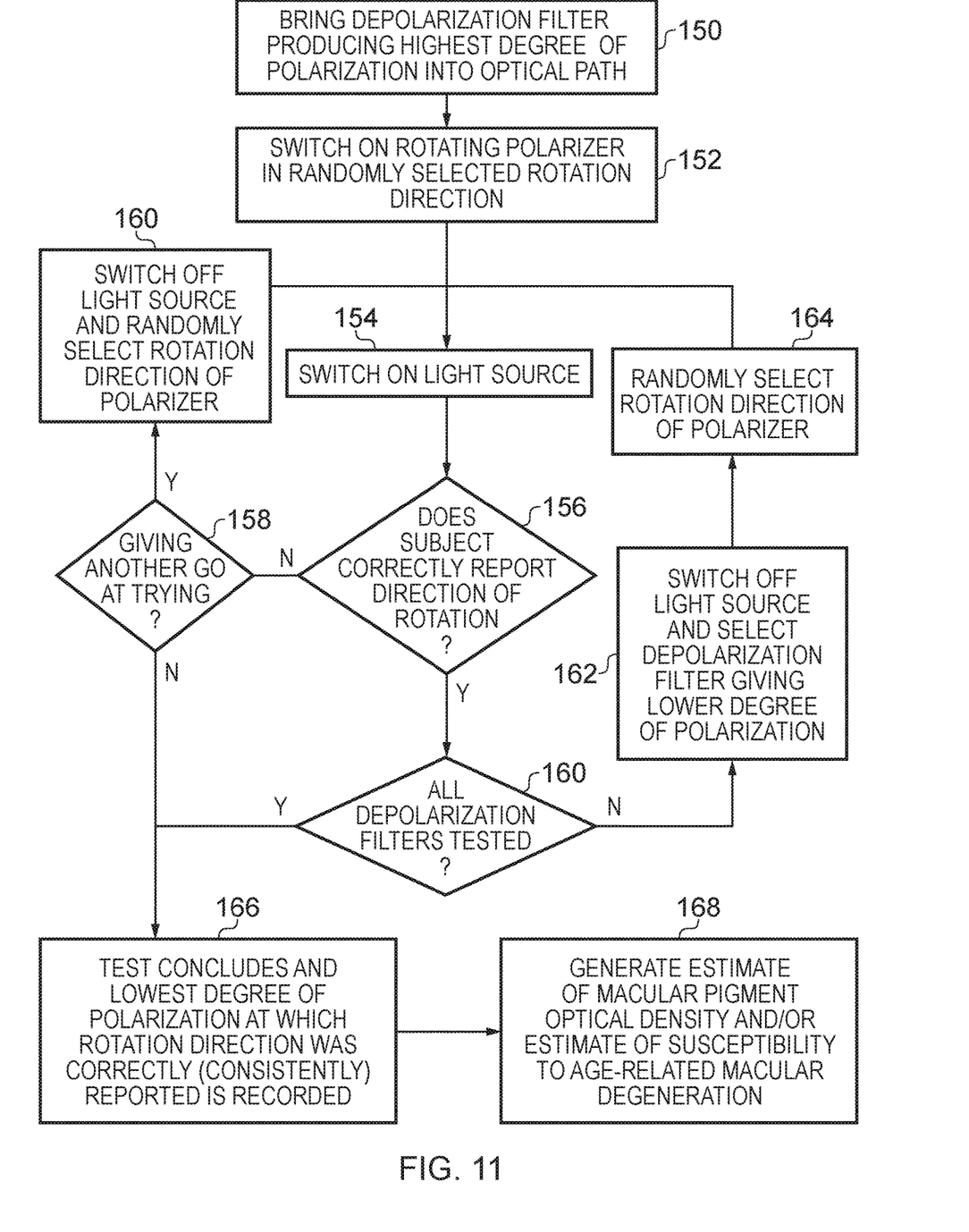
FIG. 11 shows a sequence of steps that are carried out according to the method of one example embodiment.

FIG. 11 shows a sequence of steps that are carried out according to one example embodiment of a method according to the present techniques. As mentioned above with respect to FIG. 10, these steps will typically be carried out in part by a user of the apparatus and in part under the automated control of, say, a microcontroller such as item 120 in FIG. 9. The flow begins at step 150 where a depolarization filter producing the highest degree of polarization available in the system is brought into the optical path. As mentioned above, this maximum polarization filter may essentially be a transparent component. At step 152 the rotating polarizer is switched on in a randomly selected rotational direction. Then at step 154 the light source (in this example the LED panel 102 shown in FIG. 9) is switched on. It is then determined at step 156 if the subject is able to correctly report the direction of rotation. In this example embodiment the subject is allowed another chance to attempt to correctly report the direction of rotation and thus if at step 156 they do not correctly report the direction of rotation the flow can proceed once from step 158 to step 160 where the light source is switched off and a rotational direction of the polarizer is again randomly selected. The flow then returns to step 154 where the light source is switched on again and to step 156, where it is determined if the subject is able to correctly report the direction of rotation. If, however, they remain unable to correctly report this direction, then at this iteration from step 158 the flow proceeds to step 166 where the test concludes (described in more detail below). Returning to a consideration of step 156, whilst the subject is able to correctly report the direction of rotation the flow proceeds to step 160, where it is determined if all available depolarization filters in the apparatus have now been tested. When they have, then the flow also proceeds to step 166. However, whilst further depolarization filters are available then the flow proceeds from step 160 to step 162 where the light source is switched off and a depolarization filter giving a lower degree of polarization is selected. At step 164 a direction of rotation of the polarizer is randomly selected and the flow then returns to steps 154 and 156 for a determination to be made if the subject can correctly report the direction of rotation for this new depolarization filter. Once all depolarization filters have been tested or the subject is not able to correctly report the direction of rotation (even given two attempts), then at step 166 the test concludes and the lowest degree of polarization at which the rotation direction was correctly reported is recorded. The text in step 166 further notes in brackets that the reporting of the rotational direction may be required to be "consistently" correct, in that in a variant the subject may be required to correctly report the direction of rotation more than once to lend confidence to a conclusion that they are indeed able to correctly report the direction of rotation rather than merely to guess it. Finally, at step 168, the recorded lowest degree of polarization at which the rotation direction was correctly reported by the subject can be used to generate an estimate of the macular pigment optical density for the subject's eye and/or an estimate of their susceptibility to age-related macular degeneration. These estimates can be based on previously generated measurements of the correlation between the lowest degree of polarization at which the subject can observe Haidinger's brushes (i.e. correctly report the polarization rotation direction) and macular pigment optical density or susceptibility to age-related macular degeneration. For example, following the described test an ability to perceive Haidinger's brushes (HBs) at (or above) 0-15% polarization may be classified as "low risk" (of age-related macular degeneration) or high macular pigment optical density (MPOD), perception of HBs at (or above) 16-30% may be classified as medium-low risk or medium-high MPOD, perception of HBs at (or above) 31-45% may be classified as medium risk and medium MPOD, perception of HBs at (or above) 46-60% may be classified as medium-high risk and medium-low MPOD, and perception of HBs at (or above) 61-100% may be classified as high risk and low MPOD.

In brief overall summary, an apparatus and corresponding method for testing a subject's vision are provided. The apparatus comprises a polarization arrangement configured to polarize incident light and rotate an angle of polarization applied to the incident light about an axis substantially collinear with a path of the incident light. The apparatus further comprises an optical component configured to direct light onto the polarization arrangement, wherein the polarization arrangement is configured to produce light having a selected degree of polarization from multiple selectable degrees of polarization and having a rotating angle of polarization for observation by the subject. Due to the polarization of the light the subject may be able to observe the visual phenomenon known as Haidinger's brushes and moreover due to the rotation of the angle of polarization the eye's tendency to adapt away the phenomenon is counteracted, so that the effect persists and a more reliable testing of the subject can be carried out. Testing the subject's ability to perceive the phenomenon at multiple selectable degrees of polarization enables an assessment of the health of the subject's eyes to be made, and in particular may be used to estimate the subject's macular pigment optical density and the subject's susceptibility to age-related macular degeneration.

In the present application, the words "configured to . . . " or "arranged to" are used to mean that an element of an apparatus has a configuration able to carry out the defined operation. In this context, a "configuration" means an arrangement or manner of interconnection of hardware or software. For example, the apparatus may have dedicated hardware, which provides the defined operation, or a processor or other processing device may be programmed to perform the function. "Configured to" or "arranged to" does not imply that the apparatus element needs to be changed in any way in order to provide the defined operation.

Although illustrative embodiments have been described in detail herein with reference to the accompanying drawings, it is to be understood that the invention is not limited to those precise embodiments, and that various changes, additions and modifications can be effected therein by one skilled in the art without departing from the scope of the invention as defined by the appended claims. For example, various combinations of the features of the dependent claims could be made with the features of the independent claims without departing from the scope of the present invention.

The invention claimed is:

1. Apparatus for testing a subject's vision comprising:
a polarization arrangement configured to polarize incident light and rotate an angle of polarization applied to the incident light about an axis substantially collinear with a path of the incident light; and an optical component configured to direct light onto the polarization arrangement, wherein the polarization arrangement is configured to produce light having a selected degree of polarization from multiple selectable degrees of polarization and having a rotating angle of polarization while under observation by the subject.

2. The apparatus as claimed in claim 1, wherein the polarization arrangement comprises a rotation direction selection mechanism to select a direction of rotation of the angle of polarization.

3. The apparatus as claimed in claim 2, wherein the rotation direction selection mechanism comprises a user input to select the direction of rotation.

4. The apparatus as claimed in claim 2, wherein the rotation direction selection mechanism is configured to select the direction of rotation according to at least one of:
a predetermined sequence of directions of rotation; and
a randomly chosen direction of rotation.

5. The apparatus as claimed in claim 1, wherein the polarization arrangement comprises:
a rotatable polarizer; and
a depolarization arrangement, wherein the depolarization arrangement comprises multiple depolarization filters and is configured to enable a selected depolarization filter of the multiple depolarization filters to be selected and positioned in the light path to generate the selected degree of polarization.

6. The apparatus as claimed in claim 5, wherein the multiple depolarization filters are arranged in a substantially circular pattern and the depolarization arrangement is configured to be rotated to bring the selected depolarization filter of the multiple depolarization filters into the light path.

7. The apparatus as claimed in claim 1, wherein the polarization arrangement comprises multiple polarization filters, wherein the multiple polarization filters provide the multiple selectable degrees of polarization, and is configured for a selected polarization filter of the multiple polarization filters firstly to be selected and positioned in the light path and secondly to be rotated while under observation by the subject.

8. The apparatus as claimed in claim 1, further comprising:
a light combining component; and
a further optical component configured to direct light onto the light combining component;
wherein the optical component and the further optical component each further comprise a light intensity selection mechanism to cause the light combining component to produce the light having the selected degree of polarization.

9. The apparatus as claimed in claim 1, wherein the optical component is a light source configured to generate light for direction onto the polarization arrangement.

10. The apparatus as claimed in claim 9, wherein the light source is configured to generate light including a wavelength range of 400 nm to 550 nm.

11. The apparatus as claimed in claim 9, wherein the light source is configured to generate full spectrum light.

12. The apparatus as claimed in claim 9, wherein the light source is configured to generate light including blue light.

13. The apparatus as claimed in claim 1, wherein the optical component comprises a reflector configured to reflect light from an external source onto the polarization arrangement.

14. The apparatus as claimed in claim 1, further comprising an observation component configured to received polarized light from the polarization arrangement for observation by the subject.

15. The apparatus as claimed in claim 1, wherein the polarization arrangement is configured to rotate the angle of polarization in a selected direction of continuous rotation.

16. The apparatus as claimed in claim 1, wherein the polarization arrangement is configured to rotate the angle of polarization back and forth between two predetermined angular orientations.

17. The apparatus as claimed in claim 1, wherein the optical component is configured to generate light including blue light.

18. The apparatus as claimed in claim 1, wherein the optical component is configured to generate light including a wavelength range of 400 nm to 550 nm.

19. The apparatus as claimed in, claim 1, wherein the polarization arrangement comprises a depolarization arrangement comprising at least one depolarization filter arranged to receive light having a rotating angle of polarization and further arranged to generate the selected degree of polarization.

20. The apparatus as claimed in claim 19, wherein the at least one depolarization filter comprises a distribution of particles in a translucent plastic carrier.

21. The apparatus as claimed in claim 20, wherein the translucent plastic carrier is formed of a cured resin.

22. The apparatus as claimed in claim 20, wherein the particles have a mean particle size between 100 nm and 10000 nm.

23. The apparatus as claimed in claim 19, wherein the depolarization filters are arranged to change the degree of polarization without changing the ellipticity of the polarized light.

24. Apparatus for testing a subject's vision comprising:
means for rotating an angle of polarization applied to incident light about an axis substantially collinear with a path of the incident light; and
means for directing light onto the means for rotating the angle of polarization,
wherein the means for rotating the angle of polarization is configured to produce light having a selected degree of polarization from multiple selectable degrees of polarization and having a rotating angle of polarization for observation by the subject.

* * * * *